United States Patent [19]

Charnley

[11] 4,433,686

[45] Feb. 28, 1984

[54] TRIMMING AID

[75] Inventor: John Charnley, Knutsford, England

[73] Assignee: Charnley Surgical Inventions Limited, Knutsford, England

[21] Appl. No.: 307,793

[22] Filed: Oct. 2, 1981

[30] Foreign Application Priority Data

Nov. 1, 1980 [GB] United Kingdom ................ 8035185
Sep. 3, 1981 [GB] United Kingdom ................ 8126702

[51] Int. Cl.³ .......................... A61B 17/00; A61F 1/03
[52] U.S. Cl. ............................. 128/303 R; 128/92 E; 128/92 C; 3/1.912
[58] Field of Search ................ 128/303 R, 774, 92 E, 128/92 C; 3/1.912, 36; 33/174 G, 174 D

[56] References Cited

U.S. PATENT DOCUMENTS 3,512,184  5/1970  Grove ................................. 3/1.912
4,135,517  1/1979  Reale ............................. 128/303 R

FOREIGN PATENT DOCUMENTS 2823306 12/1978 United Kingdom ................ 3/1.912
1563334  3/1980 United Kingdom ................ 3/1.912
2052997  2/1981 United Kingdom ................ 3/1.912

Primary Examiner—Michael H. Thaler
Attorney, Agent, or Firm—Ross, Ross & Flavin

[57] ABSTRACT

To facilitate the trimming of flange 100 (FIG. 6) of a prosthesis 101 (FIG. 6) to fit closely into reamed out acetabulum 200 in hip bone 201, the aid comprises a body component 11 which corresponds in overall shape to socket member 102 (FIG. 6) of the prosthesis and a separate flange 13 having a protrusion 14 engageable alternatively into socket 12 in the body component 11 and socket 104 of the prothesis. The entire aid is alternately offered into the acetabulum 200 and removed for trimming its flange 13, this being repeated until a good fit of the flange 13 into the acetabulum 200 is achieved. Then, the flange 13, removed from the body component 11, is fitted to the prosthesis 101 (as in FIG. 6) and the flange 100 of the prosthesis can then be trimmed straight away accurately for fitting into the acetabulum 200.

6 Claims, 9 Drawing Figures

TRIMMING AID

This invention concerns a trimming aid for use in the trimming of an acetabular prosthesis of the kind (hereinafter referred to as "of the kind described") comprising a socket member in the form of an approximately hemispherical body having a face wherein is a socket for the reception of the head of a femoral prosthesis and around which is a surrounding flange which may be generally planar or may be shaped, for example as described in our prior United Kingdom Patent No. 1563334 (which provides for the flange to be inclined rearwardly to the body side from said face) or in our United Kingdom Patent Application No. 80 19432, published under No. 2052997 (which provides for the flange to be partly inclined rearwardly to the body side and partly forwardly away from the body, from said face).

In the fitting of such a prosthesis, which may be moulded of a tough plastics material, after the patient's acetabulum has been reamed out, the prosthesis is offered into the reamed-out cavity and consideration is given to the need to trim the flange so as to fit snugly into and grip into the mouth of the cavity. The prosthesis is then removed and the flange is trimmed, for instance using scissors, and guide rings may be incorporated into the flange to assist the trimming operation which may have to be repeated a number of times to achieve a good fit.

This trimming accordingly can constitute a time-consuming stage in the acetabular replacement operation. Moreover, since the trimming is effected by trial and error there is a significant risk of trimming off too much of the flange with the result that the prosthesis, which is an expensive component in the operation, becomes useless and a fresh prosthesis has to be used. Moreover, then the trimming procedure has to be started all over again.

An object of the present invention is to provide a trimming aid whereby the trimming of the flange of an acetabular prosthesis as aforesaid is facilitated considerably and the risk of spoiling the prosthesis is substantially eliminated.

With this object in view, the present invention provides a trimming aid, for use in the trimming of the flange of an acetabular prosthesis of the kind described, said trimming aid comprising a body component of approximately hemispherical configuration and having a face wherein is a socket (said body component corresponding in dimensions and configuration with the socket member of the acetabular prosthesis with which it is to be used) and a separate flanged component comprising a flange (said flange corresponding in dimensions and configuration to the flange of the said prosthesis) and having a central protrusion which is an interference fit into the socket of the body component of the trimming aid, whereby said body component and flange component, when put together, define an assembly of overall configuration corresponding to the acetabular prosthesis.

The body component of the trimming aid may be smooth over its external curved surface, that is to say it can be without the grooves and ridges for bonding cement which may be present on the external curved surface of the socket member of the prosthesis which is to be permanently implanted.

In order that the invention may be fully understood, it will be described further, by way of example, with reference to the accompanying drawings, in which.

Figure 4:
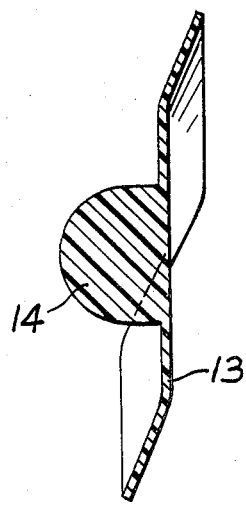
FIG. 4 is a sectional view corresponding to FIG. 2, but illustrating only the flanged component of the trimming aid.
Figure 7:
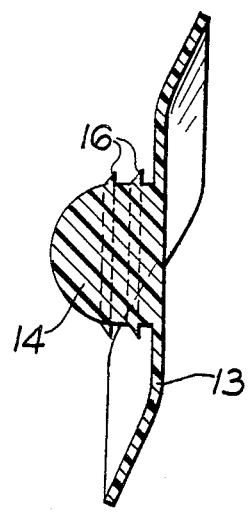
Figure 8:
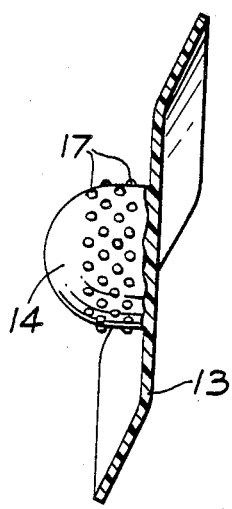
Figure 9:
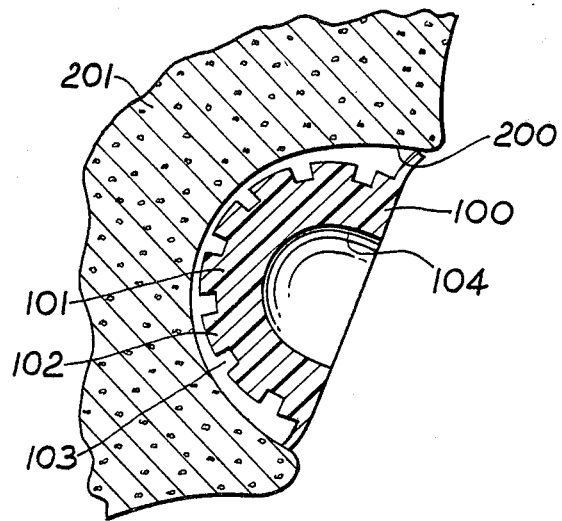

FIGS. 7 and 8 are views comparable with FIG. 4, but showing modified forms of the central protrusion of the flanged component of the trimming aid for the purpose of making more firm the temporary friction grip of the protrusion when applied into the body component of the trimming aid; and FIG. 9 shows the prosthesis after trimming by use of the trimming aid and placed in the bony acetabulum with its trimmed flange fitting the mouth of the acetabulum.

Throughout the various figures of the drawings, similar reference numerals have been allocated to similar parts.

Figure 1:
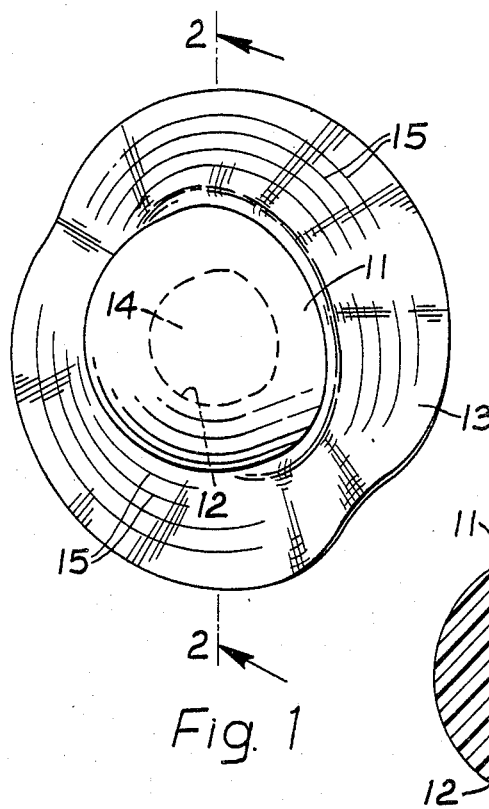
FIG. 1 is a perspective view of a preferred embodiment of the trimming aid of the invention.
Figure 2:
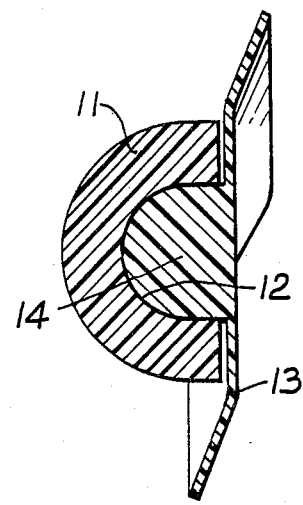
FIG. 2 is a section taken on the line 2—2 of FIG. 1.
Figure 3:
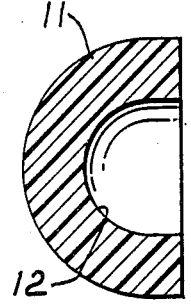
FIG. 3 is a sectional view corresponding to FIG. 2, but illustrating only the body component of the trimming aid.

Referring firstly to FIGS. 1 to 5 of the drawings, a preferred embodiment of the trimming aid of the invention comprises two separate components namely a body component indicated generally by the reference numeral 11 and illustrated in cross-section in FIG. 3, and a flanged component which is illustrated in cross-section in FIG. 4. This trimming aid is designed to facilitate the trimming of flange 100 of an acetabular prosthesis which is indicated generally by the reference numeral 101 in FIG. 6 and which forms the subject matter of our prior United Kingdom Patent Application No. 80 19432 (published under No. 2052997).

The prosthesis 101 comprises a generally hemispherical socket member 102 for cementing within a reamed-out acetabulum 200 (FIG. 5) in a patient's hip bone 201 with the flange 100 just entered into the acetabulum 200 to compress slightly, and retain, cement (not shown) provided in the acetabulum 200 to hold the prosthesis 101 in place. Annular and transverse grooves 103 are provided in the outer curved surface of the socket member 102 of the prosthesis for ensuring a good key with the cement, and a socket 104, which opens to the front face of the said socket member 102, serves in use to receive the head of a femoral prosthesis (not shown) as a form of ball and socket joint.

Figure 5:
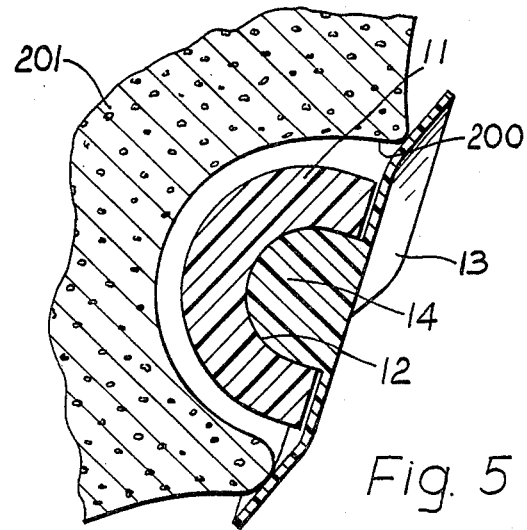
FIG. 5 is a view corresponding to FIG. 2, but illustrating the uncut trimming aid applied to the exterior of a patient's reamed-out acetabulum prior to trimming.

The trimming aid, comprising the body component 11 and the flanged component 13 assembled together as shown in FIGS. 1, 2 and 5, is of substantially the same overall configuration and dimensions as the prosthesis 101. Accordingly, the body component 11 of the trimming aid is of hemispherical configuration corresponding in shape and dimensions with the socket member 102 of the prosthesis, but, of course, because the body component 11 of the trimming aid does not have to be cemented into the acetabulum 200, there is no need to form therein any grooves corresponding to the groove 103, and the external surface of the body component 11 of the trimming aid is smooth. In the flat face of the body component 11 of the trimming aid is a respective socket 12 corresponding to the socket 104 in the prosthesis.

The flanged component of the trimming aid comprises a flange 13 of shape corresponding to the flange 100 of the prosthesis 101 and having in its middle a knob-like protrusion 14 which is a good interference fit both into the socket 104 of the prosthesis 101 (see FIG. 6) and into the socket 12 of the body component 11 of the trimming aid. The flange 13 of the trimming aid may be formed with a plurality of fine marks or guide rings, indicated at 15 in FIG. 1, moulded or embossed therein at approximately concentric dispositions around the protrusion 14, for example at two or three millimeter intervals.

The trimming aid is used as follows. Upon the patient's acetabulum being reamed out, as at 200 in FIG. 5, the fully assembled trimming aid (see FIGS. 1 and 2) is offered into the acetabulum 200 as shown in FIG. 5 and an estimate is made of how the flange 13 of the trimming aid should best be trimmed so as just to enter the acetabulum 200 and to conform to the reamed out shape of the acetabulum 200 and any irregularities thereof. The flange 13 is then trimmed and re-offered into the acetabulum 200 for checking. The trimming of the flange 13 of the aid can be performed relatively gradually and locally as desired, with the guide rings 15 facilitating this trimming, until eventually the flange 13 has been reduced to the correct external peripheral shape for fitting properly into the acetabulum 200. The trimming aid can be alternately offered back into the acetabulum 200 and removed for paring down as many times as may be necessary to achieve the required shape.

Figure 6:
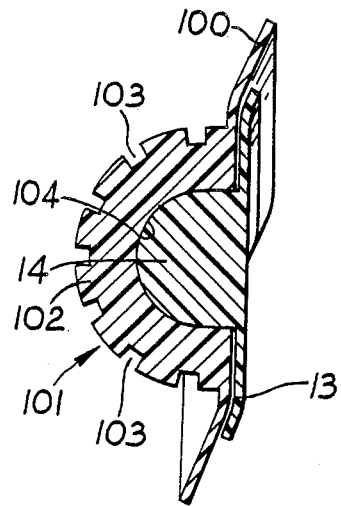
FIG. 6 is a sectional view illustrating the flanged component of the trimming aid of FIGS. 1 to 5 having been trimmed and subsequently fitted to an acetabular prosthesis for enabling the flange of the prosthesis to be trimmed to corresponding shape and size.

This having been achieved, the flanged component of the trimming aid is now separated from the body component 11 of the aid by disengaging the protrusion 14 from the socket 12 in the body component 11, whereupon, as shown in FIG. 6, the flanged component of the trimming aid is fitted to the prosthesis 101 by pressing the protrusion 14 into the socket 104 of the prosthesis, with the flange 13 of the trimming aid appropriately orientated relative to the flange 100 of the prosthesis to lie snugly and closely thereon. Thereupon, it is a relatively easy task to trim the periphery of the flange 100 of the prosthesis to correspond precisely with the trimmed periphery of the flange 13 of the trimming aid. Upon removing the flanged component of the trimming aid therefrom, the prosthesis is completely ready for cementing in place in the acetabulum 200, as shown in FIG. 9, the trimming thereof having been accurately achieved with the minimum of risk of mistake or difficulty.

Should the flange 13 of the trimming aid accidentally be trimmed back too much in a local area during the steps above described, it can, of course, be marked appropriately and a corresponding allowance can subsequently be made when trimming the flange 100 of the prosthesis. Should it transpire, e.g. as a result of accident or inappropriate estimate of the amount to be removed from the flange 13 of the trimming aid, that said flange 13 should become trimmed much too much for it to be able to be used reliably as a guide for trimming the prosthesis, then the entire flanged component of the trimming aid can be discarded and a fresh start can be made. The body component 11 does not have to be discarded and can be regarded as a reusable component. The flanged component of the trimming aid is necessarily an expendible component, and since it can be produced much more cheaply than the entire prosthesis, the spoiling of the flange 13 and the flanged component of the trimming aid represents no financial loss compared with mis-trimming and having to discard the prosthesis. This is because the trimming aid can be made of a cheap plastics material not suitable for implantation in the human body whereas the prosthesis has to be made specifically of high molecular weight polyethylene and the technology of making this complicated shape in this particular plastics material is very expensive, frequently involving machining from the solid. With the use of the trimming aid as described, mis-trimming of the prosthesis should never arise in practice.

In the flanged component as so far described, the protrusion 14 is externally-smooth and accordingly has to be quite accurately moulded to ensure that it will be a good interference fit into the socket 12 in the body component 11 of the trimming aid and in the socket 104 in the prosthesis. This accuracy can be relaxed somewhat with the alternative forms of central protrusions shown in FIGS. 7 and 8. In the arrangement of FIG. 7, two gripping ribs 16 are provided around the protrusion 14, these each being of saw-tooth configuration in radial section so that they will yield or deform very slightly when the protrusion 14 is pressed into the socket 12 or 104 and assure a reliable fit therein. Of course, there need be only a single said rib 16 instead of the two shown, or there may be more than two, according to practical limitations. Moreover the shapes of these ribs and the dispositions thereof may differ from what has been shown.

In the FIG. 8 modification, instead of the ribs 16, little protuberances 17 are provided for precisely the same purpose as the ribs 16, and whilst this figure shows a proposal for there to be four circumferential rings of such protuberances 17 any suitable array thereof can be provided.

The trimming aids, as so far described, are all suitable for use in connection with a prosthesis whose flange 100 includes a part which inclines in one direction and another part which inclines in the opposite direction, as described in our aforementioned United Kingdom Patent Application No. 80 19432 (publication No. 2052997). However, the trimming aid may include a flanged component whose flange 13 is, for example, substantially planar for use in connection with a prosthesis having a correspondingly planar flange. Moreover, the trimming aid may include a flanged component whose flange 13 is generally of a dished configuration for use with a prosthesis having a flange which is of corresponding form, being inclined rearwardly to the body side of the prosthesis, as is described in our prior United Kingdom Patent No. 1563334. Other modifications are, of course, possible.

I claim:

1. A trimming aid, for use in the trimming of the flange of an acetabular prosthesis of the kind described, said trimming aid comprising a body component of approximately hemispherical configuration and having a face wherein is a socket (said body component corresponding in dimensions and configuration with the socket member of the acetabular prosthesis with which it is to be used) and a separate flanged component comprising a flange (said flange corresponding in dimensions and configuration to the flange of the said prosthesis) and having a central protrusion which is an interference fit into the socket of the body component of the trimming aid, whereby said body component and flanged component, when put together, define an assembly of overall configuration corresponding to the acetabular prosthesis.

2. A trimming aid as claimed in claim 1 wherein the body component is smooth over its external curved surface.

3. A trimming aid as claimed in claim 1 wherein one or more protuberances are provided on the outer curved surface of the central protrusion of the flanged component of the trimming aid.

4. A trimming aid as claimed in claim 3 wherein one or more gripping ribs extend around said central protrusion.

5. A trimming aid as claimed in any preceding claim wherein the flange of the flanged component is shaped to include a part which inclines in one direction and a part which inclines in the opposite direction, to match corresponding inclined portions of the flange of the preferred form of the prosthesis.

6. A trimming aid as claimed in claims 1, 2, 3 or 4 wherein marks or guide rings are provided on the flange of the flanged component of the trimming aid to facilitate the trimming thereof.

* * * * *